(12) United States Patent
Martello

(10) Patent No.: US 9,956,310 B2
(45) Date of Patent: May 1, 2018

(54) TIME INDICATOR TAMPON

(71) Applicant: Jeannette Martello, South Pasadena, CA (US)

(72) Inventor: Jeannette Martello, South Pasadena, CA (US)

(*) Notice: Subject to any disclaimer, the term of this patent is extended or adjusted under 35 U.S.C. 154(b) by 0 days. days.

(21) Appl. No.: 14/415,338

(22) PCT Filed: Jul. 18, 2013

(86) PCT No.: PCT/US2013/051163
§ 371 (c)(1),
(2) Date: Jan. 16, 2015

(87) PCT Pub. No.: WO2014/015192
PCT Pub. Date: Jan. 23, 2014

(65) Prior Publication Data
US 2015/0217019 A1  Aug. 6, 2015

Related U.S. Application Data

(60) Provisional application No. 61/673,162, filed on Jul. 18, 2012, provisional application No. 61/750,198, filed on Jan. 8, 2013.

(51) Int. Cl.
*A61F 13/20* (2006.01)
*A61L 15/24* (2006.01)
(Continued)

(52) U.S. Cl.
CPC ............ *A61L 15/24* (2013.01); *A61F 13/202* (2013.01); *A61F 13/2074* (2013.01);
(Continued)

(58) Field of Classification Search
CPC .... A61F 13/202; A61F 13/2074; A61F 13/42; A61F 13/8405; A61F 2013/8408;
(Continued)

(56) References Cited

U.S. PATENT DOCUMENTS 5,536,507 A * 7/1996 Abramowitz ........ A61K 9/5073
424/479
5,728,125 A    3/1998 Salinas
(Continued)

FOREIGN PATENT DOCUMENTS

EP    1216673 A1    6/2002
EP    1342219 A1    9/2003
(Continued)

OTHER PUBLICATIONS

WIPO (Int'l Bureau), International Preliminary Report on Patentability for applicant's counterpart PCT application, PCT/US2013/051163, dated Jan. 20, 2015, including Written Opinion of the Int'; Search Authority. WIPO Int'l Bureau, Geneva, Switzerland.

*Primary Examiner* — Bradley Philips
(74) *Attorney, Agent, or Firm* — John D. Carpenter

(57) ABSTRACT

A tampon comprising an absorbent pledget and a time-lapse indicator associated therewith is provided. The time-lapse indicator includes a sensory material surrounded by, embedded in, covered by, or coated with a release-retarding material that protects the sensory material and prevents its release, until after a predetermined period of time has elapsed. The time-lapse indicator is located on or in the tampon or tampon removal string, or, optionally, the tampon packaging. After the time-lapse indicator is activated and a predetermined period of time has elapsed, the sensory material is released and alerts the user that it is time to change the tampon.

32 Claims, 3 Drawing Sheets

(51) Int. Cl.
*A61F 13/42* (2006.01)
*A61L 15/56* (2006.01)
*A61F 13/84* (2006.01)

(52) U.S. Cl.
CPC .......... *A61F 13/42* (2013.01); *A61F 13/8405* (2013.01); *A61L 15/56* (2013.01); *A61F 2013/8408* (2013.01); *A61F 2013/8476* (2013.01); *A61F 2013/8497* (2013.01)

(58) Field of Classification Search
CPC ..... A61F 2013/8476; A61F 2013/8497; A61L 15/24; A61L 15/56
See application file for complete search history.

(56) References Cited

U.S. PATENT DOCUMENTS

| | | | |
|---|---|---|---|
| 6,348,640 B1 | 2/2002 | Navot | |
| 6,559,772 B2 | 5/2003 | Zand | |
| 6,642,427 B2 | 11/2003 | Roe | |
| 6,713,660 B1 | 3/2004 | Roe | |
| 7,806,882 B1 | 10/2010 | Larkin | |
| 8,044,258 B2 | 10/2011 | Hietpas | |
| 8,196,809 B2 | 6/2012 | Thorstensson | |
| 8,198,504 B2 | 6/2012 | Glaug | |
| 8,247,638 B2 | 8/2012 | Kim | |
| 8,323,256 B2 | 12/2012 | Edgett | |
| 8,338,659 B2 | 12/2012 | Collins | |
| 2002/0107494 A1* | 8/2002 | Williams | A61F 13/2051 604/361 |
| 2003/0120227 A1* | 6/2003 | Williams | A61F 13/2051 604/361 |
| 2003/0235549 A1* | 12/2003 | Singh | A61C 19/063 424/70.13 |
| 2005/0124947 A1* | 6/2005 | Fernfors | A61F 13/42 604/361 |
| 2008/0033383 A1 | 2/2008 | Cantor | |
| 2010/0310475 A1* | 12/2010 | Dolhay | A61K 9/0034 424/10.3 |
| 2011/0274752 A1* | 11/2011 | Cifter | A61K 9/2077 424/465 |
| 2012/0040655 A1 | 2/2012 | Larkin | |

FOREIGN PATENT DOCUMENTS

| | | |
|---|---|---|
| EP | 2409719 A1 | 1/2012 |
| RU | 2403015 C2 | 11/2010 |
| WO | 2004028429 A1 | 4/2004 |
| WO | 2007069945 A1 | 6/2007 |

* cited by examiner

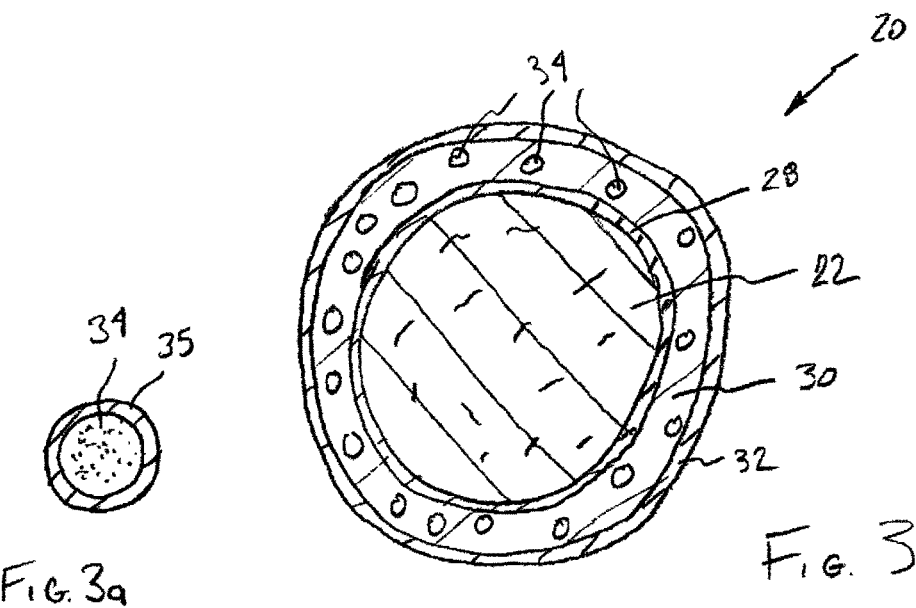
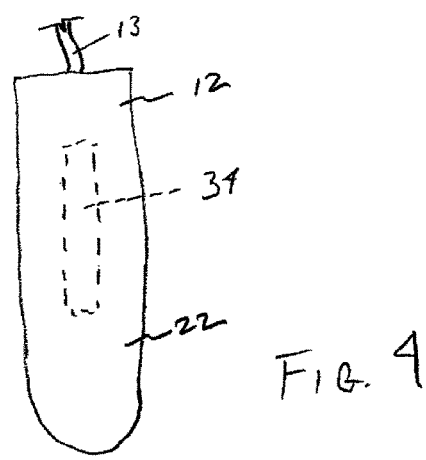

TIME INDICATOR TAMPON

CROSS-REFERENCE TO RELATED APPLICATION

This application claims the benefit of U.S. Provisional Patent Application No. 61/673,162 filed Jul. 18, 2013, the entire content of which is incorporated by reference herein.

FIELD OF THE INVENTION

The invention generally relates to catamenial devices or tampons, particularly catamenial devices or tampons adapted to notify the user when a certain period of time has transpired.

BACKGROUND OF THE INVENTION

Retained tampons are the objects most commonly left inside of a woman's vagina. It is not uncommon for a woman who suffers from a retained tampon to experience foul smelling discharge and abdominal and/or pelvic pain, dyspareunia (painful sexual intercourse), dysuria (painful urination), and palpable pelvic or vulvar masses. These symptomatic women may additionally experience fever, other constitutional symptoms such as nausea, vomiting, diarrhea, and a loss of appetite. Women afflicted with these symptoms visit their primary care physicians, gynecologists and emergency rooms, only to be embarrassingly diagnosed with a retained tampon.

A pelvic infection from a retained tampon can result in a retrograde infection in the uterus as well as in the fallopian tubes and ovaries. This type of serious pelvic infection can result in scar tissue and adhesion formation which may make an otherwise fertile woman infertile.

The most serious result of a retained tampon or a tampon left in for a longer-than-recommended period of time is that of a serious pelvic infection that can result in death from Toxic Shock Syndrome.

Given the fact that tampon strings may enter the vagina, become displaced posteriorly near the rectum, and become lost within the crevices and folds of the vulva—which can become redundant with childbearing, age and weight gain—simple self-examination may make it difficult to ascertain whether or not a tampon has been retained. The length of time that a tampon has been left inside of a woman is a consistent variable that is present in the majority of cases of Toxic Shock Syndrome.

Women forget that they have tampons in place. If the tampon capacity is exceeded, the excess menses flows, unimpeded from the vagina, to soil the user's clothing. The flow variations throughout the menstrual period do cause problems regarding how long to use or to wear a tampon.

Bypass leakage is usually not predictable by the user's habitual wearing time. Therefore, a woman is sometimes in a quandary as to how long to wear the tampon during the varying menstrual flow days.

Larger and more absorbent tampons permit a woman to change tampons less often. These more absorbent tampons are the ones that are most associated with the occurrence of Toxic Shock Syndrome.

Several patents and patent applications describe tampons having indicators for alerting the user that the absorbent capacity of the pledget is exhausted. U.S. Pat. Nos. 6,506,958 and 6,596,919, (both to Williams), U.S. Pat. No. 8,198,504 (Glaug et al.), and US 2004/0064116 (Arora et al.) are representative. None of these references describe a mechanism for alerting the user that a certain amount of time has elapsed since the tampon was inserted into the vagina. For example, the '958 patent describes a tampon 5 having an indicator 20 in contact with an absorbent pledget 10, in which the indicator contains a signal layer 16 sandwiched between an inner layer 14 and an outer layer 8. To prevent premature activation of the signal layer due to contact with moisture inherently present in the vagina, the outer layer is hydrophobic. The reference does not disclose a time-based means for activating the signal layer; rather, the signal layer is activated once it is exposed to menstrual fluid, when the pledget is at or near its absorptive capacity. The tampon described in the '919 patent operates in a similar manner, but the signal layer is located on or in the tampon removal string.

SUMMARY OF THE INVENTION

In a first aspect of the invention, there is provided a tampon that includes an absorbent pledget and an indicator adapted to alert the user that a predetermined period of time has elapsed and that it is time to remove the tampon. The indicator alerts the user by providing a physically detectable sensation, such as sight, feel or touch, or even sound, taste, or odor. In one embodiment, the indicator includes a sensory material and a time-dependent layer that covers, coats, or encapsulates the sensory material. The time-dependent layer is positioned as an inner layer, an outer layer, or as both an inner and outer layer of the tampon. Alternatively, the indicator layer is part of the tampon box, tampon inserter, tampon package, tampon removal string, or a combination of the aforementioned components. The sensory material reacts only after the passage of a predetermined amount of time, and provides a perceptible indication that the time-lapse has occurred. The perceptible indication is a color change or other visual stimulus, a physical swelling, a change in temperature or pH, a fragrance, vibration, pressure, proprioception, gas release, effervescence, a spring-open mechanism, or any combination of perceptible sensory signals.

In a preferred embodiment, the time-dependent layer is activated, or the predetermined period of time is otherwise started, upon insertion into the vagina. In a preferred embodiment, the time-dependent layer is activated, or the predetermined period of time is otherwise started, upon the opening of the tampon package, the release of the tampon from the tampon inserter, exposure to moisture, exposure to menstrual fluid, exposure to any fluid, exposure to a certain temperature or to a change in temperature, exposure to a certain pH or to a change in pH, or exposure to a certain lighting or to a change in lighting.

In another embodiment, the indicator includes a time-dependent layer that is activated by a separate device or component not attached to the tampon, by the oral ingestion of a separate and distinct substance, by the insertion rectally of a separate and distinct object not attached to the tampon, by the insertion vaginally of a separate and distinct object not attached to the tampon, by the placement on the skin of a separate and distinct object, by the user physically activating the indicator, such as the breaking of a capsule present inside of the tampon, or by the user physically activating the indicator present on the string attached to the tampon, or by the user physically activating the indicator that is part of the tampon package or tampon box.

In one embodiment, the sensory material is encapsulated, contained within a fibrous web, contained within a fiber or fibers, contained within an inert material, contained within an inert material that is absorbable, permanent or a combination of any of the above. Nonlimiting examples of sensory materials include spring-open fibers, swellable materials, heat-emitting (exothermic) materials, heat-absorbing (endothermic) materials, vibratory materials, materials that create a tingling sensation, gas-releasing materials, fragrance-releasing materials, color-changing materials (including materials that produce, eliminate, diminish, or enhance a color), materials that produce other visual indicators, microchips and nanochips (with one or more associated receivers, transducers, and/or other hardware that create a user interface), and combinations thereof.

In a second aspect of the invention, there is provided a method for avoiding retention of a tampon in a user's anatomy for longer than a predetermined period of time, that includes providing to a user a time-lapse indicator tampon as described herein, and activating the indicator which, after the predetermined period of time has elapsed, produces a signal perceptible to the user.

In a third aspect of the invention, there is provided a method that includes providing a tampon and an applicator or package and separating the tampon from the applicator or package to activate an indicator contained therein or coupled thereto. A predetermined period of time begins to run when the tampon is separated from the applicator or the package. When the predetermined period of time elapses, the user sensually perceives that the period of time has elapsed.

In a fourth aspect of the invention, there is provided a method that includes inserting a tampon into a vagina. A predetermined period of time begins to run when the tampon is inserted into the vagina. When the predetermined period of time elapses, the user sensually perceives that the period of time has elapsed.

Catamenial tampons are typically made in the form of an elongated cylinder in order that they may have a sufficiently large body of material to provide the required absorbing capacity. To ease insertion into the vaginal, the proximal end of the tampon is, generally, curved. Other shapes of tampons are also known. The tampon of the present invention may or may not be compressed, although compressed types are now generally preferred. The tampon of the present invention may be made of various fiber blends, including both absorbent and nonabsorbent fibers. Suitable absorbent fibers include, for example, cellulosic fibers such as cotton and rayon. Fibers may be 100% cotton, 100% rayon, a blend of cotton and rayon, or other absorbent materials known to be suitable for tampon use. The tampon of the present invention may or may not have a cover or wrapper. Suitable methods and materials for the production of tampons and other absorbent articles are well known to those skilled in the art.

BRIEF DESCRIPTION OF THE DRAWINGS

FIG. 3 is a cross-sectional plan view taken along line 3-3 of FIG. 1;

FIG. 3a is a cross-sectional view of the sensory material covered by a release retarding polymer;

FIG. 4 is an elevational view of a tampon in accordance with another preferred embodiment of the present invention;

DETAILED DESCRIPTION OF THE INVENTION

The following description and the drawings are illustrative of the invention, but are not limiting. Numerous specific details are described to provide a thorough understanding of various features and embodiments, but the invention is limited only by the appended claims and equivalents thereof.

Figure 1:
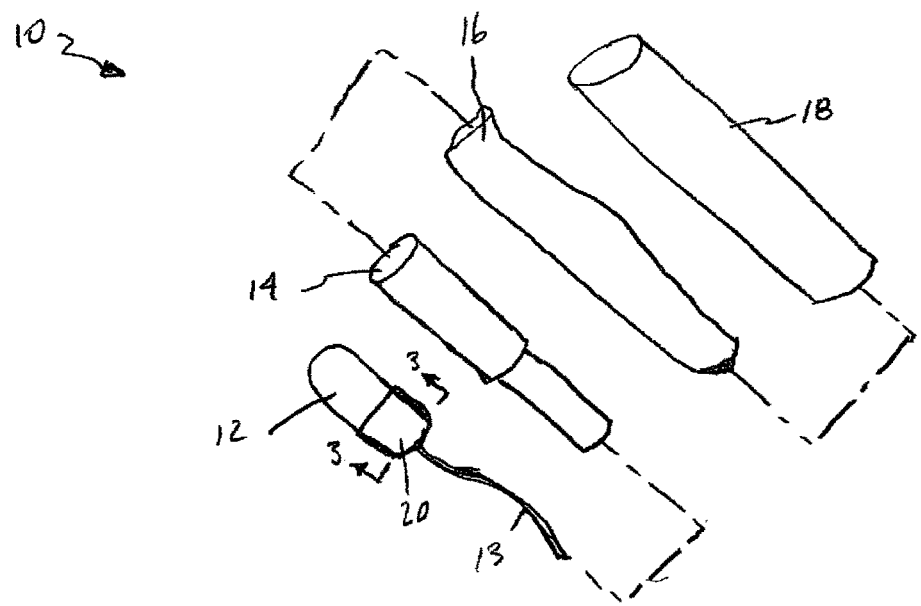
FIG. 1 is an exploded view of a tampon system in accordance with a preferred embodiment of the present invention.

FIGS. 1-6 generally show various embodiments and components of a tampon system 10 that includes a time-lapse indication or signaling feature. As shown in FIG. 1, the system 10 generally includes a tampon 12 (with a string 13), applicator 14, wrapper 16, and tube 18. Unless otherwise noted, the type of packaging is not a limitation on the present invention. Other types of tampon packaging are known in the art and are within the scope of the present invention, including, but not limited to, a tampon without an applicator.

Figure 2:
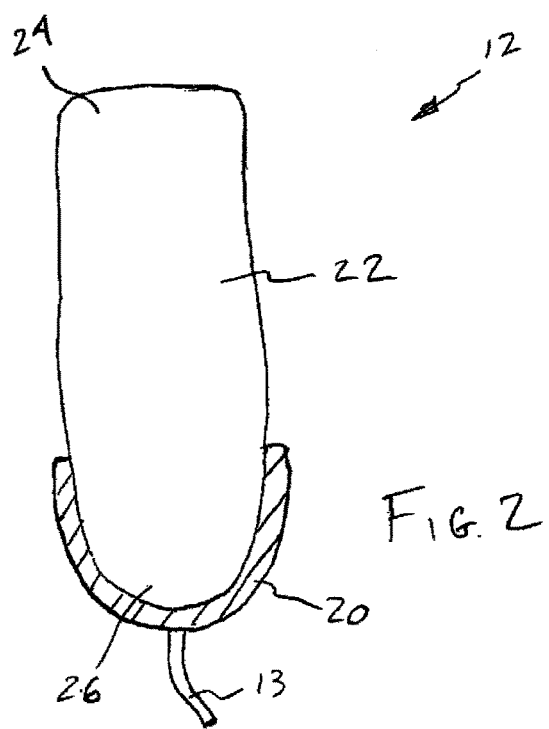
FIG. 2 is an elevational view of the tampon of FIG. 1 with the indicator in cross-section.

A preferred embodiment of a tampon system 10 that includes a time-lapse indicator 20 will now be described. As shown in FIGS. 1-3, there is provided a tampon 12 that includes an absorbent pledget 22 and the time-lapse indicator 20 associated therewith. The absorbent pledget 22 has a proximal end 24 that is placed near the cervical bone when the tampon is inserted in a woman's vagina, and a distal end 26, opposite the proximal end. The absorbent pledget is comprised of natural and/or synthetic fibers, film, foam, peat moss, or like materials. Nonlimiting examples include cellulosic fibers, such as wood pulp and cotton pulp; synthetic fibers such as polyesters and polyolefins; superabsorbent polymers, such as polyacrylic acid and the like; and other suitable materials.

In one embodiment, the indicator 20 includes or is a separate layer (or layers) that is in contact with the entire circumference of the absorbent pledget 22 at some point along the pledget's length. In another embodiment, the indicator 20 does not extend around the entire circumference, but has the form of a patch or strip. In one embodiment, the indicator 20 is located near the distal end 26 of the pledget, and extends a length from the distal end 26 to the proximal end 24 so that an effective surface area of absorbent pledget 22 is covered by indicator 20 to signal the user. In another embodiment, indicator 20 is located at the proximal end 24. In another embodiment, indicator 20 comprises a ring or band that extends around pledget 22. The indicator 20 may be located between proximal end 24 and distal end 26.

In the embodiment shown in FIGS. 1-3, the indicator 20 is affixed to the absorbent pledget 22 about its circumference. The indicator 20 is designed to provide a sensory signal to the user that a predetermined period of time has elapsed. As discussed below, the period of time can be started by a number of different mechanisms.

As shown in FIG. 3, in a preferred embodiment, the indicator 20 has an inner protective layer 28 that is positioned to contact the absorbent pledget 22; a signal layer 30 that is positioned about layer 28, either directly or indirectly; and an outer protective layer 32, positioned either directly or indirectly about layer 30. The signal layer 30 is positioned between the inner and outer layers 28 and 32, which provide structural integrity, and, in a preferred embodiment, are at least partially permeable to moisture.

The indicator 20 is activated by the elapsing of a predetermined period of time such that the actuation of the indicator is perceivable to the user while tampon 12 remains within the vagina. In a preferred embodiment, the time period is between one and ten hours, more preferably between three and eight hours, even more preferably between four and six hours. The indicator 20 becomes sensually perceptible to the user when the predetermined period of time has elapsed, thus alerting the user that it is time to remove the tampon 12.

In a preferred embodiment, the signal layer 30 is pH-activated. In general, the pH of a healthy, non-menstruating vagina is acidic, i.e., from about 3.8 to 4.5 or 5.0. Human blood, however, is slightly basic—e.g., 7.4 or 7.5. Semen has an even higher pH (7.1 to 8.0), and can alter normal vaginal pH. In a preferred embodiment of the invention, the signal layer is activated when exposed to pH 3.5 to 5.0 (non-menstruating) or, more broadly, 3.0 to 8.0 (menstruating or non-menstruating). The moisture-permeability of the inner and outer layers 28, 32 permits moisture to reach the signal layer, which can thereby be exposed to the ambient pH in the vagina.

As shown in FIG. 3, signal layer 30 has a sensory material 34 disposed therein. In a preferred embodiment shown in FIG. 3a, the sensory material 34 is a dye pellet or granule that is covered with a pH-sensitive release-retarding covering 35 that is activated—i.e., begins to dissolve or disintegrate—at pH 3.5 to 5.0. In another embodiment, the covering 35 is activated at a different pH, e.g., a pH of 3.0 to 8.0. After being exposed to the required pH, the release-retarding covering 35 is fully dissolved or disintegrated, or at least permeable to the sensory material, between 1 and 10 hours—more preferably, 3 to 4 hours—after activation. Once the covering is dissolved or disintegrated, the sensory material of the granule(s) or pellet(s) is released and thereby alerts the user that the predetermined amount of time has passed and it is time to change the tampon.

An exemplary release-retarding polymer that can be used to surround, embed, cover, or coat the sensory material 34 is a (meth)acrylic acid copolymer, such as a Eudragit® brand polymer, available from Evonik Industries, www.evonik.com. Eudragit® polymers are copolymers derived from esters of acrylic and/or methacrylic acid, whose physicochemical properties are determined by functional groups (R). Nonlimiting examples of Eudragit® polymers include Eudragit® E 100, Eudragit® E 12.5 and Eudragit® E PO. Eudragit® polymer formulations allow for custom-tailored release profiles and release over a specific period of time. Different Eudragit® RL and Eudragit® RS polymer combinations allow for custom-tailored release profiles. The Eudragit® RL polymers include Eudragit® RL 100, Eudragit® RL PO, Eudragit® RL 30 D and Eudragit® RL 12.5. The Eudragit® RS polymers include Eudragit® RS 100, Eudragit® RS PO, Eudragit® RS 30 D and Eudragit® RS 12.5. The Eudragit® NE and Eudragit® NM grade polymers do not require additional plasticizers. The Eudragit® NE polymers include Eudragit® NE 30 D and Eudragit® NE 40 D. The Eudragit® NM polymers include Eudragit® NM 30 D. Some of the Eudragit® polymers are pH-dependent polymers, such as Eudragit® E 100, Eudragit® E 12.5 and Eudragit® E PO, Eudragit® L 30 D-55, Eudragit® L 100-55, Eudragit® L 100, Eudragit® L 12.5, Eudragit® S 100, Eudragit® S 12.5 and Eudragit® FS 30 D. Both pH-dependent and pH-independent Eudragit® polymers are known. Eudragit® L 100-55 and L 30 D-55 dissolve above pH 5.5; Eudragit® L 100 and L 12.5 dissolve above pH 6.0; and Eudragit® S 100, S 12.5 and FS 30 D dissolve above 7.0. Eudragit® E PO, E 100, and E 12.5 are described as being "soluble in gastric fluid up to pH 5.0" and "swellable and permeable above pH 5.0." Gastric fluid is quite acidic, with a pH of 1 to 3 or 1.35 to 3.5. Using one or a combination of Eudragit® polymers, a release-retarding coating 35 is made to protect the sensory material 34 until the coating dissolves, disintegrates, or becomes permeable within the vagina, after the passage of a predetermined period of time. The coating has a thickness, and contains a quantity of Eudragit® polymers, sufficient to fit within the dimensional limitations of a typical tampon while ensuring that the coating dissolves, disintegrates, or becomes permeable within the vagina, after the passage of a predetermined period of time.

Nonlimiting examples of other polymers whose solubility is pH-dependent include hydroxypropyl methyl cellulose phthalate, hydroxypropyl cellulose, cellulose acetate phthalate (CAP), cellulose acetate trimellitate (CAT), Shellac, and Acryl-EZE®, a pigmented, acrylic coating system used to make enteric coatings.

In a preferred embodiment, the sensory material 34 and release-retarding covering 35 are disposed at, or just below the outer surface of the tampon 12 or indicator 20. In this way, the ambient pH of the vagina activates the release-retarding covering 35 as close in time as possible to the moment when the tampon 12 is inserted into the vagina.

Those of ordinary skill in the art will understand that once the release-retarding, pH-sensitive polymer 35 surrounding the sensory material 34 is exposed to the pH of the vagina, it begins to dissolve. Once it has dissolved, the dye pellet or other sensory material 34 is exposed and the indicator 20 or at least a portion of the tampon 12 is dyed, thus indicating that the tampon should be removed.

Nonlimiting examples of other suitable polymers (not necessarily pH-dependent) that may be used as a release-retarding coating include natural polymers, such as gelatin, chitosan, sodium carboxy methyl cellulose, sodium alginate, etc. or synthetic polymers, such as polyvinyl, polyethylene, eudragits, PEG, PVP, etc. or a combination of natural and synthetic. Other release-retarding materials are within the scope of the present invention.

In place of, or in addition to, a dye, the sensory material 34 comprises or includes a different sensation-producing material. Nonlimiting examples include other visual indicators, including materials that produce, diminish, or enhance color; heat-emitting (exothermic) materials; heat-absorbing (endothermic) materials; gas-releasing materials; fragrance-releasing materials; materials that swell; materials that spring open; materials that vibrate; and materials that create a tingling sensation perceptible to the user.

In one embodiment, the sensory material 34 comprises or includes an exothermic material that causes a warm sensation when activated or released. When the predetermined period of time has elapsed and the release-retarding covering 35 has dissolved, heat is emitted, producing a sensation of warmth and signaling the user that it is time to remove the tampon 12. An example of a suitable exothermic materials is Cabsorb ZS500A, an exothermic zeolite provided by GSA Resources Inc. Cabsorb ZS500A (Hydrated and anhydrous sodium aluminosilicate) is an agent with a high level of performance in cation exchange, adsorption, and odor control applications. The product is an odorless, dry tan powder with an average crystallite size of 2 microns. It has a large surface area, a high porosity and permeability, and a high rate of both adsorption and cation exchange. It is stable over a wide range of pH, has a high surface area and high porosity. When Cabsorb ZS500A is exposed to water, it emits heat.

In another embodiment, the sensory material 34 comprises or includes an endothermic material that causes a cold sensation when activated or released. When the predetermined period of time has elapsed and the release-retarding covering 35 has dissolved, a cold sensation is produced, signaling the user it is time to remove the tampon 12. Suitable materials that produce a cold sensation include, for example, menthol, and mixtures of menthol with ethyl alcohol. Commercially available products include Optacool®, Frescolat® ML, and Frescolat® X-cool, produced by Symrise AG. Frescolat ML® (menthyl lactate) is well tolerated in mucosal membranes. Frescolat® X-cool (menthyl ethylamido oxalate) works quickly by producing a refreshing sensation upon contact. The intense cooling effect can last up to 30 minutes. It is odorless and gentle on the skin, and especially suited for formulas with pH values of 4 to 7.

Other sensory materials that produce a cooling sensation are taught in "Cool without Menthol & Cooler than Menthol and Cooling Compounds as Insect Repellents" by John C. Leffingwell, Ph.D., updated Jul. 29, 2011, published by Leffingwell & Associates at leffingwell.com, and also in U.S. Pat. No. 7,189,760 issued Mar. 13, 2007, U.S. Pat. No. 7,030,273 issued Apr. 18, 2006, U.S. Patent Pub. No. 2008/0293821 published Nov. 27, 2008, WIPO Patent App. No. WO2008039522 published Mar. 4, 2008, U.S. Patent Pub. No. 2008/0293821 published Nov. 27, 2008, and U.S. Patent Pub. No. 2008/0038386, U.S. Patent Pub. No. 2010/0272655 published Oct. 28, 2010, U.S. Patent Pub. No. 2007/0059417 published Mar. 15, 2007, U.S. Patent Pub. No. 2007/0048424 published Mar. 1, 2007, U.S. Patent Pub. No. 2005/0265930 published Dec. 1, 2005, WIPO Patent App. WO/2008/148234 published Dec. 11, 2008, U.S. Patent Pub. No. 2006/0249167 published Nov. 9, 2006, WIPO Patent App. No. WO2006092074 published Sep. 8, 2006, WIPO Patent App. No. 2006/099762 published Sep. 28, 2006, WIPO Patent App. No. 2006103401 published Oct. 5, 2006, U.S. Patent Pub. No. 2007/0155755 published Jul. 5, 2007, WIPO Patent App. No. WO2007019719 published Feb. 22, 2007, U.S. Pat. No. 7,414,152 issued Aug. 19, 2008, U.S. Patent Pub. No. 2010/007608 published Mar. 25, 2010, WIPO Patent App. No. WO2007022651 published Mar. 1, 2007, WIPO Patent App. No. WO2007048265 published May 3, 2007, WIPO Patent App. No. WO2007104175 published Sep. 20, 2007, WIPO Patent App. No. WO2008006236 published Jan. 17, 2008, U.S. Patent Pub. No. 2008/0319055 published Dec. 25, 2008, U.S. Patent Pub. No. 2008/0311232 published Dec. 18, 2008, and U.S. Pat. No. 7,959,958 issued Jun. 14, 2011, U.S. Patent Pub. No. 2009/0054520 published Feb. 26, 2009, U.S. Patent Pub. No. 2008/0175800 published Jul. 24, 2008, U.S. Patent Pub. No. 2008/0096969 published Apr. 24, 2008, WIPO Patent Application No. WO2011061330 published May 26, 2011, and U.S. Patent Pub. No. 2011/0145970 published Jun. 23, 2011.

In another embodiment, the sensory material 34 comprises or includes a gas-releasing material. Thus, when the predetermined period of time has elapsed and the release-retarding covering 35 has dissolved, gas or gas bubbles are emitted or lapsed that produce a "fizzy" sensation signaling the user that the predetermined period of time has elapsed and it is time to remove the tampon 12. Suitable gas releasing materials include, for example, sodium bicarbonate.

In another embodiment, the sensory material 34 comprises or includes an encapsulated fragrance-releasing material. Thus, when the predetermined period of time has elapsed and the release-retarding covering 35 has dissolved, the encapsulated fragrance is emitted signaling the user that the predetermined period of time has elapsed and it is time to remove the tampon 12.

In another embodiment, the sensory material 34 comprises or includes another color changing, color reducing or color producing material. Thus, when the predetermined period of time has elapsed and the release-retarding covering 35 has dissolved, a distinct color is produced signaling the user that the predetermined period of time has elapsed and it is time to remove the tampon 12.

In another embodiment, sensory material 34 comprises or includes one or more microchips or nanochips, with suitable hardware provided in or on the tampon package (e.g.) to produce a user interface which permits the tampon user to be alerted by a signal produced by same. When the predetermined period of time has elapsed and the release-retarding covering 35 has dissolved, the microchip(s) and/or nanochip(s) produce a signal to the user that the predetermined period of time has elapsed and it is time to remove the tampon 12.

In another embodiment, the sensory material 34 comprises or includes fibers or other substances that can "spring open" or swell. Such fibers or material can be covered in a release-retarding covering 35 such that at the end of the desired time, the material is exposed and "springs open," swells or expands. Suitable fibers or materials include, for example, curly fiber, cellulosic sponge, a swellable absorbent material such as a super absorbent polymer (SAP) or hydrogel, or any combination of these materials. The "opening" or swelling of these materials in indicator 20 or tampon 12, and the resulting sensation of pressure, signal the user that the predetermined period of time has elapsed. A suitable super absorbent fiber includes, for example, a cross-linked acrylate copolymer fiber.

In another embodiment of the invention, the sensory material 34 is comprised of PA-free borage seed oil, evening primrose oil, angelica extract, coleus forskholii extract, theobromine, and the anti-oxidants vitamin C and vitamin E.

In another embodiment of the invention, the sensory material 34 is comprised of propylene glycol, aloe barbadensis (aloe leaf) juice, polysorbate 20, hydroxyethylcellulose, hamamelis virgiana (witch hazel) distillate, methylsothiazolinone, phenethyl alcohol, PPG-2 methyl ether mentha piperita (peppermint) oil, menthyl lactate, arginine HCL, ornithine HCL, water, alcohol, certified organic lycium barbarum (goji berry) fruit extract, certified organic cymbopogon shoenanthus (lemon grass) leaf/stem extract and certified organic aloe barbadensis (aloe) leaf extract.

In another embodiment of the invention, the sensory material 34 is comprised of water (eau), mineral oil, cetyl alcohol, glyceryl stearate, PEG-100 stearate, cetearyl alcohol, polysorbate 60, menthol, xanthan gum, carbomer, triethanolamine, potassium sorbate, sodium benzoate, sodium saccharin, sucralose, diazolidinyl urea and disodium EDTA.

In another embodiment of the invention, the sensory material 34 is comprised of water, SD Alcohol-39C, glycerin, carbomer, triethanolamine, menthol, peppermint, and aspartame.

In another embodiment of the invention, the sensory material 34 is comprised of glycerin, water, hydroxpropyl, guar hydroxypropyltrimonium chloride, hydroxyethylcellulose, panax ginseng (root water) extract, benzyl alcohol benzoic acid, sorbic acid, phenoxyethanol, methylparaben, ethylparaben, propylparaben and butylparaben.

In another embodiment of the invention, the sensory material 34 is comprised of water, hydroxyethylcellulose (cotton), aloe barbadensis, natural tocopherols (vitamin E), cyamopsis (guar gum), peppermint oil, sweet almond oil, menthol, citric acid (citrus fruits), certified organic extracts of flax, hibiscus, green tea and sunflower.

In another embodiment of the invention, the sensory material 34 is comprised of water, propylene glycol, sorbitol, hydroxyethylcellulose, benzoic acid, polysorbate 60, menthyl lactate and methyl salicylate.

In another embodiment of the invention, the sensory material 34 is comprised of cyclopentasiloxane, cyclotetrasiloxane, dimethiconol, dimethicone, peppermint (mentha piperita) and oleoresins capsicum.

In another embodiment of the invention, the sensory material 34 is comprised of water, cyclopentasiloxane, glycerin, cetearyl alcohol, menthyl lactate, polysorbate 60, cyclohexasiloxane, dipalmitoyl hydroxyproline, palmitoyl oligopeptide, ethylhexyl palmitate, dimethicone, tribehenin, sorbitan isostearate, sucralose, hydroxyethylcellulose, tetrasodium EDTA, sodium benzoate, methylparaben and propylparaben.

In another embodiment of the invention, the sensory material 34 is comprised of propylene glycol, cetyl hydroxyethlycellulose, purified water, menthol, niacin, I-citrulline and methylparaben.

In another embodiment of the invention, the sensory material 34 is comprised of propylene glycol, cetyl hydroxyethylcellulose, purified water, menthol, niacin, I-citrulline, methylparaben and tromethamine.

In another embodiment of the invention, the sensory material 34 is comprised of glycerin propylene glycol, water, sucrose, polysorbate 80, methyl salicylate, cinnamal, arginine, ornithine, serenoa serrulata fruit extract, turnera diffusa leaf extract, arnica montana flower extract, sodium saccharine, sodium benzoate and citrus sinesis dulcis (orange) peel oil.

In another embodiment of the invention, the sensory material 34 is comprised of water, propylene glycol, alcohol denat., polysorbate 80, hydroxyethylcellulose, arginine, citric acid, methylparaben, potassium sorbate, xanthan gum, menthol, sodium saccharine, disodium EDTA, dioscorea villosa (wild yam root extract), serenoa serrulata fruit extract, turnera diffusa leaf extract, arnica montana flower extract, angelica polymorpha sinesis root extract, cimicifuga racemosa root extract and ornithine.

In another embodiment of the invention, the sensory material 34 is comprised of water, sucrose, glycerin, alcohol denat., polysorbate 80, carbomer, xanthan gum, menthol lactate, sodium hydroxide, potassium sorbate and sodium saccharine.

In another embodiment of the invention, the sensory material 34 is comprised of purified water, cetyl alcohol, mineral oil, glyeryl stearate, sodium laurel sulfate, isopropyl myristate, aloe barbadensis leaf juice & menthol, triethanolamine carbomer, saccharin, phenoxyethanol, methylparaben, butylparaben, ethylparaben and propylparaben.

In another embodiment of the invention, the sensory material 34 is comprised of water, glycerin, polysorbate 60, carbomer, potassium acesulfame, sodium hydroxide, menthoxypropanediol, diazolidinyl urea, sodium benzoate and potassium sorbate.

In another embodiment of the invention, the sensory material 34 is comprised of caprylic/capric triglyceride, tridecyl trimellitate, beeswax, hydrogenated palm glycerides, hydrogenated palm kernel glycerides, theobroma cacao (cocoa) seed butter, menthol, butyrospermum parkii (shea butter), tocopheryl acetate, glyceryl undeclyenate, prunus amygdalus dulcis (sweet almond) oil, vitis vinifera (grape) seed oil, tocopherol and mentha piperita (peppermint oil).

In another embodiment of the invention, the sensory material 34 is comprised of aloe vera, deionized water, glycerin, sodium laureth sulfate, cetyl esters, stearic acid, sweet almond oil, sorbitol, methyl salicylate, methylparaben, propylparaben, potassium sorbate, sodium benzoate, sodium citrate, flavor and tetrasodium EDTA.

In another embodiment of the invention, the sensory material 34 is comprised of caprylic/capric triglyceride, tridecyl, trimellitate, beeswax, hydrogenated palm glycerides, hydrogenated palm kernel glycerides, theobroma cocoa (cocoa) seed butter, menthol, butyrosperimum parkii (shea butter), tocopheryl acetate, propylparaben, prunus amygdalus dulcis (sweet almond) oil, vitis vififera (grape) seed oil, tocopherol, benzyl alcohol, linalool and hydroxycitronellal.

In another embodiment of the invention, the sensory material 34 is comprised of water, propylene glycol, arginine, hydroxyethylcellulose, lactic acid, PEG-40, hydrogenated castor oil, isopulegol and methylparaben.

In another embodiment of the invention, the sensory material 34 is comprised of sweet almond oil, grape seed oil, beeswax, shea butter, caprylic/capric triglyceride, cocoa seed butter, menthol, macadamia ternifolia seed oil, peppermint oil, tocopheryl acetate, soybean oil, avocado oil, jojoba seed oil, isobornyl acetate, bisabolol, phenoxyethanol, wheat bran extract, matricaria flower extract, fucus vesiculosis extract, calendula officinalis lower extract bht, linoleic acid, limonene and linalool.

In another embodiment of the invention, the sensory material 34 is comprised of almond oil, coconut oil, beeswax, shea butter, menthol, peppermint oil, citrus essential oils, methyl paraben, BHT and ginseng.

In another embodiment of the invention, the sensory material 34 is comprised of L-arginine, niacin and glyceryl.

In another embodiment of the invention, the sensory material 34 is comprised of menthol, L-arginine and black cohosh.

In another embodiment of the invention, the sensory material 34 is comprised of PA-free borage seed oil, evening primrose oil, angelica extract, coleus forskholii extract, theobromine, and the anti-oxidants vitamin C and vitamin E.

In another embodiment of the invention, the sensory material 34 is comprised of purified water, L-arginine, menthol, maca, Korean ginseng, ginkgo biloba, damiana extract, wild yam extract 15%, epimedium extract, guarana seed, carbomer, extract, triethanolamine, propyl paraben, propylene glycol and methyl paraben.

In another embodiment of the invention, the sensory material 34 is comprised of water, mineral oil, cetyl alcohol, glyceryl stearate, PEG-100 stearate, cetearyl alcohol, polysorbate 60, menthol, xanthan gum, carbomer, triethanolamine, potassium sorbate, sodium benzoate, sodium saccharin, sucralose, diazolidinyl urea and disodium EDTA.

In another embodiment of the invention, the sensory material 34 is comprised of water, menthol, L-arginine, niacin, ginkgo biloba leaf extract, panax ginseng root extract, paullinia cupana (guarana) seed extract, dioscorea villosa (wild yam) root extract, turnera diffusa (damiana) leaf extract, pfaffia paniculata (suma) root extract, zingiber oficinale (ginger) root extract, menthe piperita (peppermint) leaf extract, aloe barbadensis (aloe vera) leaf extract, xanthan gum, hydroxyethylcellulose, citric acid and sodium hydroxide.

In another embodiment of the invention, the sensory material 34 is comprised of sweet almond oil, cinnamon cassia, natural tocopherols (vitamin E), silica, phenoxyethanol, ethylhexyglycerin and rosemary oil extract.

In another embodiment of the invention, the sensory material 34 is comprised of dimethicone, cyclopentasiloxane, dimethiconol, phenyl trimethicone, tocopheryl acetate and peppermint extract.

In another embodiment of the invention, the sensory material 34 is comprised of water, glycerin, helianthus annuus (sunflower) seed oil, triethanolamine, acrylates/C10-30 alkyl acrylate cross polymer, mentha piperita (peppermint) oil, menthyl lactate, methylisothiazolinone, phenethyl alcohol, PPG-2-methyl ether, prunus amygdalus dulcis (sweet almond) oil, tocopheryl acetate (vitamin E), arginine HCl, daucas carota sativa (carrot) oil, alcohol, certified organic lycium barbarum (goji berry) fruit extract, certified organic cymbopogon schoenanthus (lemon grass) leaf/stem extract and certified organic aloe barbadensis (aloe) leaf extract.

In another embodiment of the invention, the sensory material 34 is comprised of L-arginine, menthol, damiana, maca, ginseng and ginkgo biloba.

In another embodiment of the invention, the sensory material 34 is comprised of L-arginine HCl, motherwort, wild yam, damiana leaf, ginkgo biloba, suma root, peppermint leaf, vitamin A, vitamin C and vitamin E complex, hyaluronic acid and aloe vera gel.

In another embodiment of the invention, the sensory material 34 is comprised of Angelica pubescens root and other Angelica species, Angelica archangelica, Angelica sinensis, Angelica sylvestris, Angelica officinalis, archangel, European angelica, garden Angelica, Angelica acutiloba, preferably Angelica pubescens which is also known as Du Huo or Du Huo Radix. Angelica root is preferred, but other parts of the plants can be used as well. Angelica contains a wide and complex variety of different constituents, of a defined and undefined nature. Preferred bioactive compounds are flavonoids, flavones and coumarins, preferably, osthole or 7-methoxy-8-(3-methylpent-2-enyl) coumarin and alpha-angelicalactone. Other coumarins, include, e.g., meranzin hydrate, nodakentin, marmesinin, columbianadin, columbianetin, bergapten, heramandiol, 6-alkylcoumarins, angelol-type coumarins, byak-angelicin, ferulin, oxypeucedanin, umbelliprenin, imperatorin, neobyakangelicin, prenylcoumarins, glabralactone, anpubesol, angelical, angelin, furanocourmins, and derivatives thereof. Other bioactive agents include, e.g., linoleic acid, osthenol, falcarindiol, numerous flavonoids, and flavones, 11(S), 16(R)-dihydroxyoctadeca-9Z, 17-diene-12,14-diyn-1-ylacetate, xanthotoxin, umbelliferone, ferulic acid, magnesium, and derivatives thereof.

In another embodiment of the invention, the sensory material 34 is comprised of Coleus forskohlii extract, vinpocetine and other naturally-occurring cyclic guanine monophosphate (cGMP), phosphodiesterase (PDE) inhibitors, ferulic acid, magnesium, ascorbyl palmitate, capric triglyceride, caprylic triglyceride, silica and equivalents thereof. Coleus forskohlii comprises a diverse and complex mixture of compounds, e.g., diterpenes, and derivatives thereof. A preferred bioactive diterpene compound is forskolin and related diterpenes.

In another embodiment of the invention, the sensory material 34 is comprised of Borago officinalis; acetic acid; alkaloids; allantoin; amabiline; arabinose; ascorbic-acid; beta-carotene; bomesitol; calcium; choline; cobalt; dhurrin; fat; fiber; galactose; gamma linolenic acid; glucose plant; intermedine; lycopsamine; magnesium; malic acid; mucilage; niacin; phosphorus potassium; protein; pyrrolizidines; resin; riboflavin; silicic acid; sodium; supinine; supinine viridiflorate; thiamin and zinc. The borage plant (e.g., leaves, roots, and seeds) comprises a complex mixture of defined and undefined constituents, including, e.g., acetic acid; alkaloids; allantoin; amabiline; arabinose; ascorbic-acid; beta-carotene; bomesitol; calcium; choline; cobalt; 50 dhurrin; fat; fiber; galactose; gamma linolenic acid; glucose plant; intermedine; lycopsamine; magnesium; malic acid; mucilage; niacin; phosphorus potassium; protein; pyrrolizidines; resin; riboflavin; rosmarinic acid; silicic acid; sodium; supinine; supinine viridiflorate; thiamin and zinc.

In another embodiment of the invention, the sensory material 34 is comprised of other sources of GLA that can be utilized, including, e.g., purified or isolated GLA, botanical extracts, such as evening primrose oil (e.g., Oenothera biennis and Oenothera lamarckiana), black currant oil, spirulina, oils from the seeds of the Ribes family, etc.

In another embodiment of the invention, the sensory material 34 is comprised of vinpocetine (eburnamenine-14-carboxylic acid ethylester) and derivatives thereof. Vinpocetine is a naturally-occurring product found, e.g., in vinca minor (periwinkle). It can be extracted from natural sources, such as vinca, or produced synthetically.

In another embodiment of the invention, the sensory material 34 is comprised of one or more of the following ingredients, e.g., borage seed oil, Angelica pubescens root, Coleus forskohlii extract, magnesium and its salts, ferulic acid, vinpocetine, and equivalents thereof, in any binary, trinary, etc., combination. Such ingredients can be present in synergistic amounts.

Examples of topical compositions include, e.g., binary combinations, such as an effective amounts of borage seed oil, and Angelica pubescens root; effective amounts of borage seed oil, and Coleus forskohlii extract; effective amounts of Angelica pubescens root, and Coleus forskohlii extract; and quarternary combinations, such as effective amounts of borage seed oil, Angelica pubescens root, Coleus forskohlii extract, and vinpocetine. Such compositions can further comprise pharmaceutically-acceptable excipients, skin and mucosal penetration enhancers, etc. In preferred embodiments, included as excipients are, e.g., de-ionized water (e.g. about 0.5-50%, preferably 5% concentration), Span 80 (sorbitan monooleate (e.g., 0.2-20%, preferably 2%, concentration), lecithin (e.g., egg or soy phosphatidyl-choline (e.g. 0.2-20%, preferably 2% concentration), lavender for body oils by Flavor and Fragrance Specialties (0.06-1.25%, preferably 0.25%), Blackberry Musk for body oils by Flavor and Fragrance Specialties 0.1-2.5% preferably 0.5%) or other flavors and fragrances, glycerin (e.g., 2-10% w/w), saccharin or other sweetening agents, and monosodium Gaunosine Mono Phosphate (flavor enhancer), silica, ferulic acid and other forms of ferulate, magnesium sulfate and other forms of magnesium, vitamin E acetate and other forms of tocopherol, and ascorbyl palmitate and other forms of ascorbic acid along with other anti-oxidants and stability enhancers. Ingredients, and amounts of ingredients, can be adjusted such that the compositions possess minimal irritation to the female reproductive organs. Ingredients can also be included that enhance the cosmetic appeal (e.g., enhancing the smell, feel, etc.) of the compositions, but which are inert as far as enhancing the sensory response, e.g., enhancing the smell, feel, etc., of a composition.

In another embodiment of the invention, the sensory material 34 is comprised of a quaternary topical composition, which comprises, on a w/w basis, e.g., a) 10-99% borage seed oil and/or evening primrose oil; b) 0.001-99% Angelica pubescens, c) 0.001-8% Coleus forskohlii, and d)

0.001-8% vinpocetine. This composition can further comprise, e.g., e) magnesium (0.001-90%), and f) ferulic acid (0.001-10%).

It will be understood that the sensory material 34 can comprise any combination of and any composition of any of the components described or listed herein.

It will be understood by those skilled in the art that the sensory material 34 can operate in two different ways. In some embodiments, the sensory material 34 is encapsulated (as described below) or coated with a release-retarding polymer (as described above), such that once the predetermined period of time elapses, the sensory material 34 is released and the user is signaled that it is time to remove the tampon 12. In other embodiments, the sensory material 34 is released when the predetermined period of time begins, but it does not actually signal the user until the predetermined period of time elapses. For example, using four hours as an exemplary predetermined period of time, in an embodiment where the sensory material 34 is dye that is positioned in the core of the tampon (see FIG. 4), the material encapsulating the dye is broken at the beginning of the predetermined period of time. This may be done for example similar to the way the core of a light stick is broken to mix the chemicals and cause illumination. The material of the pledget 22 is chosen so that it takes four hours for the dye (or other sensory material 34) to penetrate from the core to the outer layer of the pledget 22, thereby signaling the user that it is time to remove the tampon 12. For example, the material may be a woven material that takes approximately four hours for the dye to penetrate from the core to the bottom of the tampon 12, where it would be perceived by the user. In another embodiment, the pressure inside the vagina activates the sensory material 34 or otherwise starts the predetermined period of time elapsing.

In one embodiment, the sensory material 34 is encapsulated in a soft gel, which begins to dissolve upon the occurrence of a triggering event, such as being in the presence of the desired pH, a desired temperature or a desired moisture level or a combination of these factors. Moreover, the soft gel is comprised of enough material that it continues to dissolve during the predetermined period of time, such that at the end of the predetermined period of time, the sensory material 34, such as a dye, is emitted from the soft gel, thus providing an indication to the user that the predetermined period of time has elapsed and it is time to remove the tampon 12.

When the sensory material is not a fiber, the signal layer may include a fibrous web having sensory material 34 incorporated therein.

As shown in FIG. 4, in another embodiment, the sensory material 34 is disposed inside the tampon 12. In another embodiment, the sensory material 34 (dye, exothermic material, cooling agent, etc.) is embedded in or scattered throughout the release-retarding covering 35.

Figure 5:
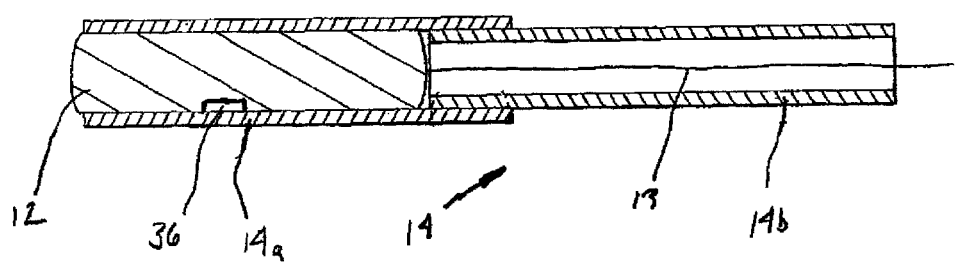
FIG. 5 is a cross-sectional elevational view of a tampon in an applicator in accordance with another preferred embodiment of the present invention.
Figure 6:
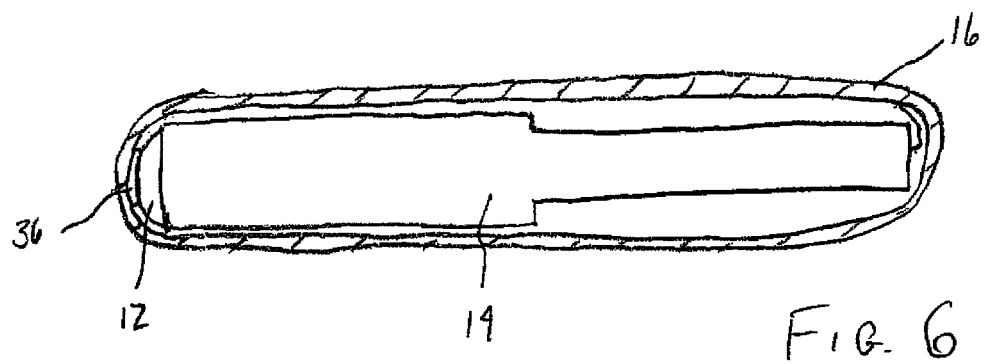
FIG. 6 is a cross-sectional elevational view of a tampon and, applicator in a wrapper in accordance with another preferred embodiment of the present invention.

With reference now to FIGS. 5-6, in another embodiment, the system 10 includes components or methods such that the period of time begins elapsing when the tampon 12 is removed from or otherwise exits the applicator 14, wrapper 16, tube 18 or other type of packaging. For example, as shown in FIG. 5, the tampon 12 or applicator 14 includes a tab 36 or the like that is broken when the tampon 12 is moved longitudinally along the inside of the applicator 14. The breaking of the tab 36 (or two mating tabs) starts the period of time. In other words, when tampon 12 is separated from the applicator 14, the predetermined period of time begins to elapse. At the end of the predetermined period of time, sensory material 34 is released signaling the user that the predetermined period of time has elapsed and it is time to remove the tampon 12. In another embodiment, the predetermined period of time is started by a connection that is broken between the telescoping outer 14a and inner 14b tubes of the applicator. For example, when any of the connections or tabs (e.g., tab 36) discussed herein is broken, a chemical or the like is released that interacts with and begins to dissolve the release-retarding covering 35 surrounding or embedded within the sensory material 34.

As shown in FIG. 6, in another embodiment, the tab 36 or connection may be positioned between the wrapper 16 and tampon 12. As described above, when the tab 36 (or two mating tabs) are broken (or the wrapper 16 and tampon 12 are otherwise separated), the predetermined period of time begins. At the end of the predetermined period of time, sensory material 34 is released signaling the user that the predetermined period of time has elapsed and it is time to remove the tampon 12.

In still another embodiment of the invention, the string 13 is comprised of, coated by, contains, or otherwise includes sensory material 34 and/or a release-retarding covering 35. Or, the string 13 includes a signal layer, as described above. In this embodiment, both the string 13 and the tampon 12 include a sensory material 34, or just the string 13 includes the sensory material 34. In another embodiment, there is a plastic capsule or the like positioned at the junction of the tampon 12 and the string 13. Once the tampon 12 has been positioned within the vagina, the user can collapse or otherwise break the capsule (by pinching the capsule, pulling the string, etc.) to release the sensory material 34 and/or activate the release-retarding covering 35 to start dissolving.

EXAMPLE 1

A hard gelatin capsule is used as a carrier of the sensory material. The hard gelatin capsule is inserted into the tampon just underneath its surface. The capsule is formulated as follows. Cabsorb ZS500A powder is deposited into a hard gelatin capsule and the joint between the upper and lower parts of the capsule is sealed before any film coating is applied. This is important since the critical site for the intactness of the film to the capsule and for its resultant functionality is located at the joint between the upper and lower parts of the capsule. A subcoat of hydroxypropylcellulose (HPC) is first sprayed onto the capsule to optimize the adhesion of the Eudragit® film to the hard gelatin capsule shell. The HPC precoating formulation is prepared with 63.4 grams of the polymer, Klucel EF (HPC) and 640.6 grams of water. The polymer content and solids content of the spraying suspension are 9.0% respectively. Both the solids and polymers applied equal to 4.0 mg/cm$^2$. First, two thirds of the water is heated to greater than 50 degrees Celsius. Next, the Klucel EF (HPC) is added to the water with a gentle stirring action. This formulation is then mixed for 60 minutes. The remaining water is then added and cooled down to below 35 degrees Celsius. Next, the pH-sensitive Eudragit® coating is formulated. The formula is comprised of the following ingredients: 528.0 grams of Eudragit® L 30 D-55, 31.7 grams of triethyl citrate, 6.7 grams of polysorbate 80 (33% aqueous) and 395.1 grams of water. The polymer content of the spraying suspension is equal to 16.5%. The solids content of the spraying suspension is equal to 20.0%. The polymer applied with this formulation is 10.0 mg/cm$^2$ and the solids applied with this formulation is 12.1 mg/cm$^2$. The pH-sensitive Eudragit® coating is made by diluting Eudragit® L30 D-55 with water. Next, triethyl citrate and polysorbate 80 (33% aqueous solution) are both added while gently stirring with a conventional stirrer. The usual amount of polymer formulated using this method will equal 4 to 6 mg/cm² surface although higher quantities may be necessary depending on the application.

Conventional or modified coating pans are used to apply the HPC precoating and Eudragit® coating. The capsule shells should not be prewarmed to temperatures above 25 degrees Celsius so as to prevent the capsule from becoming brittle due to loss of moisture. Spray suspension is accomplished by the use of spray guns used with peristaltic pumps to regulate the spray rate. It is important for the spray suspension to be stirred throughout the spraying process to prevent the solid constituents from settling. To prevent solid constituent settling, the pump tube should have the smallest possible diameter. Product temperature should be maintained at 25 to 28 degrees Celsius during the spray process to ensure that a homogenous film layer is obtained. A prolonged drying process should be avoided to prevent the formation of a brittle capsule shell.

Capsules used may have the following characteristics: 2.5 kg hard gelatin capsules with a length of 12.1 mm, a weight of 348.0 mg, and a surface of 220.1 mm². The spray suspension will be comprised of 704 grams of precoating HPC suspension and 961.5 grams of Eudragit® suspension to 10.0 mg polymer weight gain/cm². Precoating HPC conditions include atomizing pressure of 2.0 bar, drying air volume of 0.84 m³/min, inlet air temperature of 45 degrees Celsius, product bed temperature of 25 to 28 degrees Celsius, pump speed of 5 min, coating time of 160 min, and a spray rate of 1.8 grams/min/kg capsules. Eudragit® coating conditions include a drying air volume of 0.84 m³/min, an inlet air temperature of 27 to 30 degrees Celsius, a product bed temperature 20 degrees Celsius, a pump speed of 6 min, atomizing pressure of 0.8 bar, coating time of 215 min, and spray rate of 1.8 g/min/kg capsules.

EXAMPLE 2

A hard gelatin capsule is used as a carrier of the sensory indicator, Frescolat® ML. Frescolat® ML is a cyclic terpene: [1R-[1.alpha.(R*), 2.beta., 5.alpha.]]-5-Methyl-2-(1-methylethyl)cyclohexyl lactate ($C_{13}$—$H_{24}$—$O_3$), with a molecular weight of 228.37 g/mol. The hard gelatin capsule is inserted into the tampon just underneath its surface. The capsule is formulated as follows. Frescolat® ML crystalline powder is deposited into the hard gelatin capsule and the joint between the upper and lower parts of the capsule is sealed before any film coating is applied. This is important since the critical site for the intactness of the film to the capsule and for its resultant functionality is located at the joint between the upper and lower parts of the capsule. A subcoat of hydroxypropylcellulose (HPC) is first sprayed onto the capsule to optimize the adhesion of the Eudragit film to the hard gelatin capsule shell. The HPC precoating formulation is prepared with 63.4 grams of the polymer, Klucel EF (HPC) and 640.6 grams of water. The polymer content and solids content of the spraying suspension are 9.0% respectively. Both the solids and polymers applied equal to 4.0 mg/cm². First, two thirds of the water is heated to greater than 50 degrees Celsius. Next, the Klucel EF (HPC) is added to the water with a gentle stirring action. This formulation is then mixed for 60 minutes. The remaining water is then added and cooled down to below 35 degrees Celsius. Next, the pH-sensitive Eudragit® coating is formulated. The formula is comprised of the following ingredients: 528.0 grams of Eudragit® L 30 D-55, 31.7 grams of triethyl citrate, 6.7 grams of polysorbate 80 (33% aqueous) and 395.1 grams of water. The polymer content of the spraying suspension is equal to 16.5%. The solids content of the spraying suspension is equal to 20.0%. The polymer applied with this formulation is 10.0 mg/cm² and the solids applied with this formulation is 12.1 mg/cm². The pH-sensitive Eudragit® coating is made by diluting Eudragit® L30 D-55 with water. Next, triethyl citrate and polysorbate 80 (33% aqueous solution) are both added while gently stirring with a conventional stirrer. The usual amount of polymer formulated using this method will equal 4 to 6 mg/cm² surface although higher quantities may be necessary depending on the application.

Conventional or modified coating pans are used to apply the HPC precoating and Eudragit® coating. The capsule shells should not be prewarmed to temperatures above 25 degrees Celsius so as to prevent the capsule from becoming brittle due to loss of moisture. Spray suspension is accomplished by the use of spray guns used with peristaltic pumps to regulate the spray rate. It is important for the spray suspension to be stirred throughout the spraying process to prevent the solid constituents from settling. To prevent solid constituent settling, the pump tube should have the smallest possible diameter. Product temperature should be maintained at 25 to 28 degrees Celsius during the spray process so as ensure that a homogenous film layer is obtained. A prolonged drying process should be avoided to prevent the formation of a brittle capsule shell.

Capsules used may have the following characteristics: 2.5 kg hard gelatin capsules with a length of 12.1 mm, a weight of 348.0 mg and a surface of 220.1 mm². The spray suspension will be comprised of 704 grams of precoating HPC suspension and 961.5 grams of Eudragit® suspension to 10.0 mg polymer weight gain/cm². Precoating HPC conditions include atomizing pressure of 2.0 bar, drying air volume of 0.84 m³/min, inlet air temperature of 45 degrees Celsius, product bed temperature of 25 to 28 degrees Celsius, pump speed of 5 min, coating time of 160 min, and a spray rate of 1.8 grams/min/kg capsules. Eudragit® coating conditions include a drying air volume of 0.84 m³/min, an inlet air temperature of 27 to 30 degrees Celsius, a product bed temperature 20 degrees Celsius, a pump speed of 6 min, atomizing pressure of 0.8 bar, coating time of 215 min, and spray rate of 1.8 g/min/kg capsules.

In other embodiments, the time-lapse indicator features described above can be applied to other wearable or usable items that should be removed after a certain period of time. For example, sanitary napkins, panty liners, diapers, incontinence pads, contraceptive sponges and other intra-uterine devices, such as rings, diaphragms, etc. can include a feature such that a user or wearer experiences a sensory perception after a predetermined period of time has elapsed. Typically, sanitary napkin articles fall into two distinct categories, those worn externally in contact with the perineum and those worn internally, partially or wholly contained within the vaginal canal. External sanitary protection products include, without limitation, panty liners, full-size pads and ultrathins. All of the descriptions above that apply to the tampon embodiments are hereby incorporated by reference and are applicable to sanitary napkins, diapers, training pads, training pants, undergarment pads, sanitary protection products, panty shields, incontinence pads and incontinence products, absorbent underpants, baby wipes and body wipes, absorbent tissues, medical garments, absorbent drapes, medical wipes, face masks, air filtration media, air freshener products, disposable odor absorbent sheets, bed sheets, surgical gowns, full-size pads, ultrathins, panty liners aka pantiliners, diapers, incontinent undergarments, incontinent devices, medical bandages, wound dressings, band-aids, healthcare related products, dental tampons, medical tampons, surgical tampons, nasal tampons, nasal packings, nasal pads, feminine hygiene products, personal care absorbent products, barrier birth control devices, contraceptive sponges, vaginal rings, pessaries, tablets, suppositories, vaginal medicated devices, bioadhesive microparticles, creams, lotions, foams, ointments, balms, salves, boluses, pastes, solutions, gels, douches, contraceptive foams, contraceptive jellies, transdermal or topical applications and intra-uterine as well as other intra-cavitary devices or materials or absorbent bodies that can be inserted into any body cavity, and any absorbent article. An "absorbent article" refers to devices which absorb and contain body fluids, and more specifically, refers to devices which are placed against or near the skin to absorb and contain the various fluids discharged from the body.

In alternative embodiments the present invention is administered in any form by any effective route, including, but not limited to, oral, parenteral, enteral, intra-peritoneal, topical, local, dermal, transdermal, ophthalmic, trans-mucosally, nasally, via nasopharyngeal absorption, transotic, local, topical, non-oral, aerosol, inhalation, subcutaneous, intramuscular, buccal, sublingual, rectal, vaginal, transurethral, intra-arterial, rapid infusion, intravenously, long-release implants and short-release implants. Any of these routes can be used individually or in combination.

Alternative embodiments of the invention can be administered as a cream, lotion, foam, gel, jelly, spermicidal jelly, liquid, emulsion, solution, suspension, aerosolization, mist, spray, powder, suppository, tablet, device, etc.

The present invention can also be administered by or used with a device, such as a cartridge, diaphragm, pessary, intra-uterine device, contraceptive sponge, sponge, menstrual discharge collector, vaginal insert, female mechanical barrier-type device, feminine cup, feminine cap, film, coating, patch, intrauterine barrier-type device, film, lens, sponge, tampon, osmotic drug delivery device, ring or sheath. Such devices can carry the invention in any effective manner, e.g., a device can be impregnated or coated with the invention, or fitted with a carrier element, such as a film or polymeric material etc. that contains the invention. The present invention can then be inserted into the vagina where delivery is effectuated. A device can be a sponge-like structure, such as a polymeric sponge tampon, which contains the present invention. The device can also be reusable.

A composition of the present invention can also be administered by or used with a male condom, e.g., by applying the invention or sensory material to the condom prior to insertion into the vagina, e.g., in combination with other lubricants, spermicides or spermicidal jellies, or, as a dry or wet film or coating on the exterior of the condom surface.

In general, any delivery means, including devices, polymers, etc., that are used to deliver agents can be utilized in accordance with the present invention, such as means for delivering antiviral agents, bacteriocidals, contraceptives, hormones, spermicides, virucides, lubricants, chemotherapeutic agents or anti-inflammatories.

Compositions of the present invention can further comprise other active agents, including, but not limited to, e.g., contraceptive agents, spermicidal agents, such as, e.g., nonoxynol-9, octoxynol, menfegol, benzalkonium chloride, peroxygen compounds or hydrogen peroxide, bacteriocides, chemotherapeutic agents, germicides, antiviral agents, virucides, chemotherapeutic agents, vasodilators and agents which increase vaginal lubrication.

The compositions of the present invention can further comprise any pharmaceutically acceptable carrier. By the phrase, "pharmaceutically acceptable carrier," it is meant any excipient, solvent, vehicle, inert ingredient, etc., which is formulated with the active ingredients of a pharmaceutical composition, such as the standard agents described, e.g. in Remington's Pharmaceutical Sciences, Eighteenth Edition, Mack Publishing Company, 1990. Other suitable carriers are well known in the art and include, for example, water, phosphate buffered saline solutions, phosphate buffered saline containing POLYSORB 80, emulsions such as oil/water emulsion and various type of wetting agents, salt solutions, alcohols, gum arabic, vegetable oils, benzyl alcohols, aqueous vehicles, water-miscible vehicles, non-aqueous vehicles (e.g., corn oil, cottonseed oil, peanut oil, sesame oil, ethyl oleate, isopropyl myristate, and benzyl benzoate), etc. Carriers also include, e.g., milk, sugar, certain types of clay, silica, gelatin, stearic acid or salts thereof, magnesium, magnesium stearate and other forms or salts of magnesium, or calcium stearate, talc, vegetable fats or oils, gums, glycols, propylene glycol, buffers, antimicrobial agents, preservatives, flavor, fragrance and color additives, gelatin, carbohydrates such as lactose, amylose or starch, talc, silicic acid, viscous paraffin, perfume oil, fatty acid monoglycerides and diglycerides, pentaerythritol fatty acid esters, hydroxymethylcellulose and the like. Other additives include, e.g., antioxidants and preservatives, coloring, flavoring and diluting agents, emulsifying and suspending agents, such as acacia, agar, alginic acid, sodium alginate, bentonite, carbomer, carrageenan, carboxymethylcellulose, cellulose, cholesterol, fatty acids, triglycerides and esters of fatty acids, fatty alcohols, gelatin, hydroxyethyl cellulose, hydroxypropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, transdermal enhancers (ethanol, propylene glycol, water, sodium oleate, leucinic acid, oleic acid, capric acid, sodium caprate, capric/caprylic triglyceride, silica, lauric acid, sodium laurate, neodecanoic acid, dodecyl-amine, cetryllactate, myristyllactate, lauryllactate, methyllaurate, phenyl ethanol, hexa-methylene lauramide, urea and derivatives, dodecyl N,N-dimethylamino acetate, hydroxyethyllactamide, phyophatidylcholine, sefsol-318 (a medium chain glyceride), isopropyl myristate, isopropyl palmitate, palmitic acid, several surfactants, including polyoxyethylene (10) lauryl ether (Brij 361 R), diethyleneglycol lauryl ether (PEG-2-L), laurocapram (Azone; 1,1 dodecylazacycloheptan-2-one), acetonitrile, 1-decanol, 2-pyrrolidone, N-methylpyrrolidone, N-ethyl-1-pyrrolidone, 1-Methyl-2-pyrrolidone, 1-lauryl-2-pyrrolidone, sucrose monooleate, dimethylsulfoxide (DMSO) about 80% concentration required, decylmethyl-sulfoxide (n) enhances primarily polar or ionic molecules (soluble in ethanol), acetone, polyethylene glycol 100-400 MW, dimethylacetamide, dimethylformamide, dimethylisosorbide, sodium bicarbonate, various N7_16-alkanes, mentane, menthane, menthol, terpinene, D-terpinene, dipen-tene, N-nonalool and limonene, skin penetration enhancers (e.g., lecithin), and miscellaneous ingredients such as microcrystalline cellulose, citric acid, dextrin, dextrose, liquid glucose, lactic acid, lactose, magnesium chloride, potassium metaphosphate, starch, and the like.

In another embodiment of the present invention, the tampon or other wearable or usable item includes a pH-dependent polymer, a temperature-dependent polymer, a time-dependent polymer or a combination of these polymers (e.g., release-retarding covering 35 that surrounds a pharmacologically active material). The pharmacologically active material may be selected from the group consisting of antimicrobials, antioxidants, antiparasitic agents, antipruritics, astringents, local anesthetics and anti-inflammatory agents may be incorporated. Alternatively, the pharmacologically active material may be integrated within the pH-dependent polymer, within a temperature-dependent polymer, within a time-dependent polymer or within a combination of the aforementioned polymers. In another embodiment, the pharmacologically active material is integrated with the sensory material 34 and surrounded by, embedded in, covered by, or coated with the release-retarding covering 35.

As is known in the art, many different compounds or compositions have been used to inhibit the production and/or propagation of the toxin that has been implicated with Toxic Shock Syndrome as well as with the growth of bacteria (e.g., including, but not limited to, *Staphylococcus Aureus* bacteria) as well as other pathogens (referred to herein as an "inhibitor composition" or "inhibitor compositions"). In another embodiment of the present invention, the tampon or other wearable or usable item includes a pH-dependent polymer, a temperature-dependent polymer, a time-dependent polymer or a combination of these polymers (e.g., release-retarding covering 35) that surrounds an inhibitor composition. Alternatively, an inhibitor composition is integrated within the pH-dependent polymer, within a temperature-dependent polymer, within a time-dependent polymer or within a combination of these polymers. In another embodiment, the inhibitor composition is integrated with the sensory material 34 and surrounded by the release-retarding covering 35. Nonlimiting examples of inhibitor compositions include a pharmaceutically acceptable carrier and alkyl polyglycoside; cellulose acetate phthalate; antibacterial agents such as clindamycin, erythromycin, lysostaphin, neomycin, penicillin, phenol, PHMB, sulfonamide, tetracycline, triclosan, and/or quaternary ammonia compounds; biostatic agents such as gentian violet and methylene blue; an antibacterial agent that is a mixture of alkyl dimethyl benzylammonium chloride and alkyl dimethyl ethylbenzylammonium chloride; a finishing agent that is comprised of one or more polyoxyethylene fatty acid esters; an antibacterial compound that consists of a mixture of polyvinylpyrrolidone as an absorptive agent and iodine as an antibacterial agent; an antibacterial compound that contains zinc, mercury or penicillin, erythromycin or nitrofurazone; an inhibitor composition, such as cerulenin, hexachlorophene, thiolactomycin, thiomalonate or triclosan; an active ingredient such as myreth-3-myristate or glycerol monolaurate; the first active ingredient of an inhibitor composition that is selected from the group consisting of hexachlorophene, benzylparaben, benzyl salicylate, benzophenone-6, benzophenone-7, benzophenone-8, benzophenone-9, benzophenone-10, benzophenone-12, benzophenone-1, benzophenone-2, benzophenone-3, chlorophene, 2,4-diaminodiphenylamien, dichlorophene, HC Green No. 1, HC Orange No. 1, HC Red No. 1, triclosan, isopropylbenzylsalicylate, and phenyl salicylate; the second active ingredient of an inhibitor composition that is selected from the group consisting of 2-phenylethanol, benzyl alcohol, trans-cinnamic acid, 4-hydroxybenzoic acid, methyl ester, 2-hydroxybenzoic acid, 2-hydroxybenzamide, acetyl tyrosine, 3,4,5-trihydroxybenzoic acid, lauryl 3,4,5-trihydroxybenzoate, phenoxyethanol, 4-hydroxy-3-methoxybenzoic acid, para-aminobenzoic acid and acetaminophen; the second active ingredient of an inhibitor composition that is selected from the group consisting of laureth-3, laureth-4, laureth-5, PPG-5 lauryl ether, 1-0-dodecyl-rac-glycerol, sodium laureth sulfate, potassium laureth sulfate, disodium laureth (3) sulfosuccinate, dipotassium laureth (3) sulfosuccinate and polyethylene oxide (2) sorbitol ether; the second active ingredient of an inhibitor composition that is selected from the group consisting of sodium lauryl sarcosinate, lauramide MEA, lauramide DEA, lauramidopropyl dimethylamine, disodium lauramide MEA sulfosuccinate, and disodium lauroamphodiacetate and mixtures thereof and where the cationic moiety of said carboxyl salt is selected from sodium, potassium or both and where the cationic moiety of said sulfonate salt is selected from sodium, potassium or both; the second active ingredient of an inhibitor composition that is selected from the group consisting of glycerol monolaurate, myreth-3-myristate or TEA laureth sulfate; an isoprenoid compound that is comprised of polyisoprenoid; an isoprenoid compound that is a terpene compound which is an acylic terpene and/or a cylic terpene and/or a hemiterpene and/or a monoterpene and/or a sesquiterpene; an isoprenoid compound that is selected from a group consisting of geraniol, cis-terpin, trans-terpin, terpineol, alpha-terpinene, beta-terpinene, delta-terpinene, gamma-terpinen, beta-myrcene, dipentene, alpha-myrcene, menthol, 2-methyl-6-methylene-1,7-octadiene, linalool, alpha-ionone, beta-ionone, alpha-pinen, beta-pinene, nerol, campher, citral a, nerolidol, farnesol, phytol, alpha-carotin, beta-carotin and limonene; a part of an inhibitor composition that is selected from a group consisting of caprylic acid, capric acid, lauric acid, myristic acid, palmitic acid and stearic acid; a part of an inhibitor composition that is an aliphatic alcohol selected from the group consisting of glycerol, glycol, sucrose, glucose, sorbitol, and sorbitan; a part of an inhibitor composition that is selected from the group consisting of an alcohol polyalkoxylated sulfate salt and polyalkoxylated sulfosuccinate salt; a part of an inhibitor composition that is a glycol selected from the group consisting of ethylene glycol, propylene glycol, polypropylene glycol, and combinations thereof; an alkyl polyglycoside, that is selected from the group consisting of Glucopon 220, Glucopon 225, Glucopon 425, Glucopon 600, Glucopon 625, and TL 2141; a part of an inhibitor composition that is derived from a saturated or unsaturated fatty acid; a part of a compound having a cationic moiety selected from the group consisting of sodium, potassium and combinations thereof; a part of an inhibitor composition that comprises an amine selected from the group consisting of lauramine, lauramino proprionic acid, sodium lauriminodipropionic aid, lauric hydroxyethyl imidazoline, lauryl hydroxyethyl imidazone and mixtures thereof; an inhibitor composition that additionally comprises an additive selected from the group consisting of myreth-3-myristate, glycerol monolaurate, laureth-4, ascorbic acid, sodium bisulfite, and vitamin E; one or more organic acids selected from the group consisting of citric, glycolic, malic, tartaric and lactic acids, in combination with at least one of the group consisting of oligomer and polymer derivatives of said acids, said oligomer and polymer derivatives of said acids, said acids and derivatives and there is also present a suitable hydrolytic enzyme that will hydrolyze such acids into the monomeric form; along with the use of physiologically safe organic acids, the addition of sodium benzoate or sodium propionate to further prevent bacterial growth in combination with the acid(s); an effective amount of a protein or fragment or residue thereof to bind to microorganisms, said protein selected from the group consisting of fibronectin, fibrinogen, collagen, laminin and chondronectin; divalent magnesium cations where suitable salts include those of magnesium, barium, calcium or strontium or of other divalent cations such as zinc, manganese, copper, iron, nickel and the like; a suitable salt is magnesium stearate or magnesium acetate; a pharmaceutical composition comprised of sodium cholate, dimethylpolysiloxane emulsion, hydroxymethylpropylcellulose, benzalkonium chloride, nonoxynol 9 and water; an inhibitor composition selected from the group consisting of hexahydro beta acids, hexahydro beta salts, tetrahydroiso alpha acids, and tetrahydroiso alpha salt; glycerol monolaurate; an oxygen inhibiting agent or "oxygen inhibitor," a reducing agent, a free radical scavenger, an antioxidant, or some other agent that displaces oxygen; common synthetic antioxidants that include butylated hydroxyanisole (BHA), butylated hydroxytoluene (BHT), propyl gallate (PG) and tertiary butylhydroquinone (TBHQ); natural antioxidants that include mixed tocopherols, citric acid, ascorbic acid (vitamin C), ascorbyl palmitate and erythorbic acid; other antioxidants that include thiodipropionic acid and salts, sodium and potassium bisulfite, sodium sulfite, and sodium and potassium metabisulfite; other oxygen inhibiting agents such as vitamin E, N-acetylcysteine and beta-mercaptoethanol; a surface active agent that is selected from the group consisting of glycerol, polysorbate 40, polysorbate 60, polysorbate 80, PPG-5-laureth-5, PPG-8-stearate, polyethylene glycol and polypropylene glycol; a pre-toxin limiting agent or a toxin enclosing agent; antifouling agents such as Furanones and L-acyl homoserine lactones; a temperature limiting agent or a temperature equilibrium agent; a quorum sensing compound that is a peptide; antimicrobial agents and/or biostatic agents; ascorbic acid, ascorbic salts and ascorbic esters; antioxidant materials such as tocopherols (including vitamin E), sterically hindered phenol (BHT) and those materials that are readily oxidized, such as sulfites, ascorbic acid, ferrous sulfate and stannous chloride and those that can absorb oxygen (e.g. by chemisorption), such as porphyrins; oxygen scavenging materials that include ascorbic acid, vitamin E, ferrous sulfate, stannous chloride or any of a variety of well known, safe oxygen scavengers; an antioxidant that is selected from the group consisting of sterically hindered phenols; an additive selected from the group consisting of myreth-3-myristate, glycerol monolaurate, laureth-4, ascorbic acid, sodium bisulfite and vitamin E; an inhibitor composition that includes an aliphatic alcohol selected from the group consisting of glycerol, ethylene glycol, propylene glycol, polyethylene glycol, polypropylene glycol, sucrose, glucose, sorbitol and sorbitan and wherein the cationic moiety of said sulfate salt and said sulfosuccinate salt are selected from the group consisting of sodium, potassium and combinations thereof; wherein the isoprenoid compound is selected from the group consisting of cis-terpin, trans-terpin, beta-terpinene, thujone, gamma-carotene, delta-carotene, lutein, and violaxanthin; an inhibitor composition in which the first active ingredient is cis-terpin, trans-terpin and combinations thereof; a part of an inhibitor composition that has a third active ingredient comprising an ether, ester, amide, glycosidic or amine bond linking a C8-C18 fatty acid to an aliphatic alcohol or to a polyalkoxylated sulfosuccinic salt; an inhibitor composition that is glycerol monolaurate; an inhibitor composition that is Monomuls 90 L-12 with glyceryl dilaurate and glyceryl monolaurate and mixtures thereof; an inhibitor composition where the fatty acid is lauric acid; an inhibitor composition that includes polyhydric alcohol; an inhibitor composition that includes the polyhydric alcohol glycerol; an inhibitor composition that is Lauricidin; an inhibitor composition in which the active ingredient is glyceryl monocaprylate, glyceryl caprate, glyceryl monocaprylate, glyceryl caprate, glyceryl monomyristate, glyceryl palmitate, glyceryl monostearate, glyceryl monooleate and/or glyceryl monopalmitate and a combination thereof.

In another embodiment, the tampon or other article includes one or more odor-absorbing agents, such as activated charcoal, sodium bicarbonate, clay, zeolites, and combinations thereof.

In an alternative embodiment, the process can further comprise encasing a second portion of the absorbent material with a liquid impermeable material, to prevent the collected fluid from transferring completely through the article. Liquid impermeable materials include, without limitation, polymeric films or coatings, such as polyolefins (e.g. polyethylene and polypropyelene), polyvinyls (e.g. polyvinyl acetate, polyvinyl chloride, and polyvinylidene chloride), copolymers (e.g. ethylene vinyl acetate), and blends or laminates of one or more of the above polymers; bodily fluid repellent structures such as nonwovens, aperture films, and repellent fiber layers integrated into the bottom layer of the absorbent materials.

Nonlimiting examples of substrates that can be used include absorbent and non-absorbent fibers, such as cellulose, rayon, polyester, polyethylene, polypropylene, ethylene vinyl acetate, polyurethane, and the like; non-woven fabrics, such as spunbonded fabric, thermal bonded fabric, resin bonded fabric, and the like; aperture and non-apertured films; foams such as polyurethane foams; and superabsorbent polymers, such as polyacrylic acid, and the like.

It should be understood that the present invention can be used with or administered to any suitable subject, preferably human females, but also to females of other species, such as apes, monkeys, chimpanzees, pets, such as dogs, cats, rats, hamsters, and mice, horses, pigs, cows, sheep, and other domestic or wild animals, and males of any species. By the term "administering," it is meant that a composition is delivered to the subject in such a way that it can achieve the desired purpose.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," and any variant thereof, means any connection or coupling, direct or indirect, between two or more elements.

The disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize.

What is claimed is:
1. A tampon comprising:
an absorbent pledget, having a proximal end and a distal end; and
a time-lapse indicator coupled to or associated with the absorbent pledget, the time-lapse indicator comprising a sensory material at least partially surrounded by, embedded in, covered by, or coated with a release-retarding material that protects the sensory material and prevents its release until after a predetermined period of time has elapsed, wherein the release-retarding materal comprises a pH sensitive polymer that begins dissolving or disintegrating after being exposed to a pH of 3.0 to 8.0.

2. The tampon recited in claim 1, wherein the pH-sensitive polymer comprises a copolymer derived from esters of acrylic acid and/or methacrylic acid.

3. The tampon recited in claim 1, wherein the release-retarding materal is selected from the group consisting of hydroxypropyl methyl cellulose phthalate, hydroxypropyl cellulose, cellulose acetate phthalate, cellulose acetate trimellitate, and mixtures thereof.

4. The tampon recited in claim 1, wherein the predetermined period of time is 1 to 10 hours.

5. The tampon recited in claim 1, wherein the predetermined period of time is 3 to 8 hours.

6. The tampon recited in claim 1, wherein the predetermined period of time is 4 to 6 hours.

7. The tampon recited in claim 1, wherein the sensory material is selected from the group consisting of visual indicators, heat-emitting materials, heat-absorbing materials, gas-releasing materials, fragrance-releasing materials, vibrating materials, materials that swell or spring-open, materials that produce a tingling sensation, and mixtures thereof.

8. The tampon recited in claim 1, wherein the time-lapse indicator is affixed to the absorbent pledget.

9. The tampon recited in claim 8, wherein the time-lapse indicator is in affixed to the absorbent pledget near the proximal end of the pledget.

10. The tampon recited in claim 8, wherein the time-lapse indicator is in affixed to the absorbent pledget near the distal end of the pledget.

11. The tampon recited in claim 8, wherein the time-lapse indicator is in contact with the entire circumference of the absorbent pledget at some point along the length of the pledget.

12. The tampon recited in claim 1, wherein the time-lapse indicator comprises a first protective layer, a second protective layer, and a signal layer disposed between the first and second protective layers, and wherein the signal layer comprises or contains the sensory material.

13. The tampon recited in claim 12, wherein one or both of the first and second protective layers comprise a pH-sensitive polymer.

14. A tampon comprising:
   an absorbent pledget, having a proximal end and a distal end; and
   a time-lapse indicator coupled to the absorbent pledget, the time-lapse indicator comprising a signal layer sandwiched between first and second protective layers, wherein at least one of the first and second protective layers is adjacent to the absorbent pledget, and wherein the signal layer comprises a sensory material at least partially surrounded by, embedded in, covered by, or coated with a release-retarding material that protects the sensory material and prevents its release until after a predetermined period of time has elapsed.

15. The tampon recited in claim 14, wherein one or both of the first and second protective layers comprise a pH-sensitive polymer.

16. The tampon recited in claim 14, wherein the release-retarding material comprises a pH-sensitive polymer.

17. The tampon recited in claim 16, wherein the pH-sensitive polymer comprises a copolymer derived from esters of acrylic acid and/or methacrylic acid.

18. The tampon recited in claim 16, wherein the pH-sensitive polymer is selected from the group consisting of hydroxypropyl methyl cellulose phthalate, hydroxypropyl cellulose, cellulose acetate phthalate, cellulose acetate trimellitate, and mixtures thereof.

19. The tampon recited in claim 16, wherein the pH-sensitive polymer begins dissolving or disintegrating after being exposed to a pH of 3.0 to 8.0.

20. The tampon recited in claim 14, wherein the predetermined period of time is 1 to 10 hours.

21. The tampon recited in claim 14, wherein the predetermined period of time is 3 to 8 hours.

22. The tampon recited in claim 14, wherein the predetermined period of time is 4 to 6 hours.

23. The tampon recited in claim 14, wherein the sensory material is selected from the group consisting of visual indicators, heat-emitting materials, heat-absorbing materials, gas-releasing materials, fragrance-releasing materials, vibrating materials, materials that swell or spring-open, materials that produce a tingling sensation, and mixtures thereof.

24. A tampon comprising:
   an absorbent pledget, having a proximal end and a distal end; and
   a tampon removal string coupled to the absorbent pledget, wherein the string comprises one or more fibers surrounded by, embedded in, covered by, or coated with a time-lapse indicator, the time-lapse indicator comprising a sensory material and a release-retarding material that protects the sensory material and prevents its release until after a predetermined period of time has elapsed.

25. The tampon recited in claim 24, wherein the release-retarding material comprises a pH-sensitive polymer.

26. The tampon recited in claim 25, wherein the pH-sensitive polymer comprises a copolymer derived from esters of acrylic acid and/or methacrylic acid.

27. The tampon recited in claim 25, wherein the pH-sensitive polymer is selected from the group consisting of hydroxypropyl methyl cellulose phthalate, hydroxypropyl cellulose, cellulose acetate phthalate, cellulose acetate trimellitate and mixtures thereof.

28. The tampon recited in claim 26, wherein the pH-sensitive polymer begins dissolving or disintegrating after being exposed to a pH of 3.0 to 8.0.

29. The tampon recited in claim 24, wherein the predetermined period of time is 1 to 10 hours.

30. The tampon recited in claim 24, wherein the predetermined period of time is 3 to 8 hours.

31. The tampon recited in claim 24, wherein the predetermined period of time is 4 to 6 hours.

32. The tampon recited in claim 24, wherein the sensory material is selected from the group consisting of visual indicators, heat-emitting materials, heat-absorbing materials, gas-releasing materials, fragrance-releasing materials, vibrating materials, materials that swell or spring-open, materials that produce a tingling sensation, and mixtures thereof.

* * * * *